United States Patent [19]
Fivez et al.

[11] Patent Number: 5,602,895
[45] Date of Patent: Feb. 11, 1997

[54] PARTIALLY-TRANSPARENT-SHIELD-METHOD FOR SCATTERED RADIATION COMPENSATION IN X-RAY IMAGING

[75] Inventors: Christiaan Fivez, Antwerpen; Pieter Vuylsteke, Mortsel, both of Belgium

[73] Assignee: AGFA-Gevaert, Mortsel, Belgium

[21] Appl. No.: 346,763

[22] Filed: Nov. 30, 1994

[30]     Foreign Application Priority Data

Dec. 24, 1993  [EP]  European Pat. Off. ............. 93203671

[51] Int. Cl.$^6$ .................................................. H05G 1/64
[52] U.S. Cl. .............................................. 378/98.4; 378/7
[58] Field of Search ......................... 378/98.9, 98.4, 378/98.11, 98.12, 7

[56]                References Cited

U.S. PATENT DOCUMENTS

| | | | |
|---|---|---|---|
| 4,549,307 | 10/1985 | Macovski ............................ | 378/145 |
| 4,741,009 | 4/1988 | Yamagata et al. ..................... | 378/98.12 |

FOREIGN PATENT DOCUMENTS

| | | |
|---|---|---|
| 0157417 | 10/1985 | European Pat. Off. . |
| 3704685 | 10/1987 | Germany . |

*Primary Examiner*—Don Wong
*Attorney, Agent, or Firm*—Richard J. Birch

[57]                ABSTRACT

The disclosed methods for generating scatter-compensated radiation image are based on one irradiating shot of the object. By comparing the detected signal under a partially transparent body (ea. disk or strip), positioned between the x-ray source and the object being imaged, with the signal in the image near the border of the shadow of the partially transparent body, the radiation scatter signal in the location of the body is calculated. In case of a polychromatic source, calibration with two known materials allows accurate calculation of the radiation scatter. The partially transparent bodies are positioned at several locations in between object and source and, by means of interpolation technique, the radiation scatter in every location of interest can be calculated. The radiation scatter image is subtracted from the original image of the object. The primary signal (=without radiation scatter) in the location of the bodies has undergone an extra drop because of the body but the information about the object under the body is not lost. If necessary, in a next step the image can be restored by compensating the effect of the bodies on the primary signal.

18 Claims, 7 Drawing Sheets

PARTIALLY-TRANSPARENT-SHIELD-METHOD FOR SCATTERED RADIATION COMPENSATION IN X-RAY IMAGING

BACKGROUND OF THE INVENTION

1. Field of the Invention

The present invention relates to a method for compensating x-ray imaging systems for radiation scatter.

2. Description of the Prior Art

In x-ray imaging systems, the total flux of detected radiation consists not only of photons that did not interact with the elements of the attenuating object being imaged but also of radiation scatter. Specifically for systems using area detectors the amount of radiation scatter can be very large. For a large class of applications, such as energy-selective imaging, this radiation can be an important source of error and must be compensated in order to have satisfying results.

A lot of work has been done already in searching good methods for compensating x-ray imaging systems for radiation scatter.

The use of grids or air gaps reduces but doesn't eliminate the radiation scatter. For many applications, as for dual x-ray absorptiometry (DXA), it is not sufficient.

Several analytical models, representing the scatter—some of them use point spread functions—are proposed in the prior state of the art. They require parameters of which the values are difficult to obtain and mostly to be found experimentally. These models do not give satisfying accuracy in some applications.

In the prior state of the art, some investigators (Molloi SY, Mistretta CA. Scatter-glare correction in quantitative dual-energy fluoroscopy. Med. Phys. 1988; 15:289–297) use correction tables for a specific application that give a hypothesised relationship between the detected grey level in a certain pixel and the scatter fraction. They are for most applications rough estimations for which the accuracy is insufficient.

In the prior state of the art, (Wagner F C, Macovski A, Nishimura D. Dual-energy x-ray projection imaging: Two sampling schemes for the correction of scattered radiation, Med. Phys. 1988;15:732–748), a method is sometimes used in which two x-ray irradiations of an object are made; one with a disk sampler, consisting of an array of small lead disks above the object, and one without the sampler. In the shadow of each disk only scattered radiation is detected and the average of the pixel values in this shadow gives the value of the radiation scatter. By a fit of a low-frequency surface through the sample values of the radiation scatter, an estimation of the radiation scatter in the whole image is generated. The scatter corrected image is obtained by subtracting the scatter-surface from the second image. A disadvantage of this method is that one needs two shots of the object. In medical applications, it means that the patient (=object) receives a larger x-ray dose and that he may have moved between two shots. Switching quickly disk sampler and detectors asks for a mechanically complicated system. Another implementation of the method with the lead beam stops in which only the x-ray irradiation with the disk sampler is made has the disadvantage that all the information about the object is lost under the beam stops. This can be an important disadvantage.

In the prior state of the art, another method for scatter radiation compensation, recently proposed in the literature (Shaw C. A novel technique for simultaneous acquisition of primary and scatter image signals. SPIE Vol. 1651 Medical Imaging VI: Instrumentation (1992), p. 222–233), is the Primary-Modulation-Demodulation (PMD) technique. The primary x-ray distribution is modulated and demodulated with two filters of equal material and thickness placed on the tube and detector sides of the objects. The modulation-demodulation process results in a reduction of scatter signals in selected regions of the image. It leaves the overall primary signal distribution unchanged. The signal drop of the scatter radiation can be measured and used to estimate the scatter radiation signal in the selected regions. Although the PMD method allows both primary and scatter signals to be acquired simultaneously, it has two main disadvantages; it is unknown how the drop in scatter radiation relates to location, scattering geometry, patient, etc.. Another disadvantage is that it is practically impossible to match the modulator and the demodulators. Therefore the results are based on rough estimates and the accuracy is reduced.

SUMMARY OF THE INVENTION

Objects of the Invention

It is an object of the present invention to overcome the disadvantages of the prior art methods.

It is a further object to be able, by only one shot of the object being imaged, to calculate the scatter radiation component in the image with a high degree of accuracy, and to compensate the image of the object for this radiation scatter, without losing information about the primary radiation distribution in any location of the object.

Statement of the Invention

The above objects of the present invention are achieved by a method of generating a scatter-compensated radiographic image of an object comprising the steps of 1) exposing said object together with a shield placed between a source of radiation and said object to an amount of radiation emitted by said source so as to generate a radiation image, said shield comprising a number of bodies of a known material and of a known thickness that are partially transparent to irradiation, 2) detecting said radiation image by means of an area detector, 3) converting the detected radiation image into an electric signal representation, 4) in a number of locations of said bodies within said radiation image deriving a signal proportional to the amount of scattered radiation, 5) composing a scatter image representing in each location of the image of said object the amount of scatter present in the image by interpolation between the derived scatter signal values, 6) subtracting said scatter image from said original image so as to generate a scatter compensated radiographic image representation, 7) applying said scatter-compensated image representation to an output device for generating a visible scatter-compensated image.

A second embodiment of the method for generating a scatter-compensated radiation image in accordance with the present invention is in particular advantageous in case of an exposure of an object by means of a irradiation source emitting polychromatic irradiation.

This method comprises the steps of 1) exposing said object together with a shield comprising a number of bodies of a known material and of a known thickness that are partially transparent to irradiation, said shield being placed between an irradiation source and said object, to an amount of radiation emitted by said irradiation source, so as to generate a radiation image;

2) detecting said radiation image by means of an area detector, 3) converting the detected radiation image into an electric signal representation, 4) generating calibration data representing the attenuation of the spectrum of said source by combinations of thicknesses of different basis materials, 5) for a number of locations of said bodies estimating the scatter value on the basis of supplementary attenuation of primary irradiation photons by said bodies, 6) determining from the calibration data the thickness of body material that corresponds with the estimated scatter value, 7) if this thickness value equals the real thickness of the body then the estimated scatter value equals the real scatter value, otherwise steps (5) to (6) are repeated, 8) generating a scatter image by interpolation in between the real scatter values in said number of locations, 9) subtracting the scatter image from said radiation image so as to generate a scatter-compensated image representation, 10) applying said scatter-compensated image representation to an output device for generating a visible scatter-compensated image.

Basis materials are materials that have such characteristics that the attenuation properties of an organic material in the human body can be deduced from the attenuation caused by a combination of such basis materials.

Primary photons are photons of non-scattered transmitted radiation.

In a particular embodiment the radiation image of the combination of said object and said shield is detected by means of an area detector consisting of a photostimulable phosphor screen and wherein said radiation image is read out and converted into an electrical signal representation by scanning said screen by means of stimulating irradiation and by detecting the light emitted upon stimulation and converting the detected light into an electric signal.

By means of a partially transparent body is generally meant a body of a material that is partially transparent to the irradiation emitted by the source of irradiation (X-ray source for example) so that the partially transparent body when, together with an object being imaged, is exposed to irradiation causes a drop of the primary radiation signal, however the information of the object being imaged is not lost at the position of the body.

In the following the term 'a partially transparent shield' refers to a shield comprising a plurality of partially transparent bodies of known materials and known thicknesses (as seen by an x-ray going straight from the source through said partially transparent body to the detector).

The area of a partially transparent body is to be small enough so that the amount of scattered radiation under and in the immediate neighbourhood of said partially transparent body can be assumed to be the same.

The output device used for generating a scatter-compensated image can be a hard copy device such as a laser printer or a thermal printer; alternatively it can be a soft copy generating device such as a monitor.

The methods of the present invention are based on the following ideas:

A feature of the invention is the calculation of the scattered radiation in a specific location of the image through the use of a partially transparent body of a known material and of known thickness, placed in an imaging system between the x-ray source and the object being imaged. The area of said partially transparent body (or the width of the body if a strip is used) is small enough to assume in the image the same amount of scattered radiation under and in the immediate neighbourhood of said partially transparent body (in case a strip is used as body: under and in the immediate neighbourhood perpendicular to the strip (the strip is long compared with its width) the amount of scattered radiation is assumed to be the same). By measuring the signal in the shadow of the partially transparent body and in the immediate surroundings of it, one can calculate the radiation scatter component in the location of the partially transparent body.

The radiation intensity signal under the body is extra attenuated in comparison with the signal besides said body. In case of a monochromatic source the extra attenuation factor is known since the thickness of the partially transparent body, the type of material of said body and the photon energy of the source is known. In one embodiment of an x-ray imaging system in accordance with the invention, the radiation scatter component of the image of the object in the location of said body is then found by subtracting a signal Q from both signals detected under—and around said body. If the signal, after subtraction of Q, under the partially transparent body, divided by the signal, after subtraction of Q, around said body is equal to said extra attenuation factor, then the signal Q is the real radiation scatter component of the image in the location of said body.

In case of a polychromatic source the said extra attenuation factor can be different in different locations of the image of the object as a consequence of beam hardening. In case the photon energy spectrum is not too broad one can neglect to a certain degree the influence of beam hardening on the extra attenuation factor and estimate said extra attenuation factor in a certain location of the image based on the detected intensity in said location.

In a particular embodiment of an x-ray imaging system in accordance with the invention, which is especially useful for medical applications using conventional x-ray sources (with polychromatic x-radiation), though which is not limited to this application, calibration with two known basis materials is made to be able to calculate accurately the radiation scatter component in the image of the object. This calibration means that an image is made of a set of thickness combinations of two basis materials. This image is taken under the same circumstances (which means: same source and source parameters (spectrum), same type of detector) as the image of the object.

The following is known (Alvafez R., Macovski A. Energy-selective reconstruction in x-ray computerized tomography. Phys. Med. Biology, 1976, Vol. 21, No 5, 733–744) from the prior state of the art:

For a certain group of materials, as for all the organic materials in a human body, and for the range of photon energies used in diagnostic radiology, the x-ray attenuation properties of every thickness combination of materials can be represented by the combination of two equivalent thicknesses of two chosen basis materials.

In our case it means that in every pixel of the image, the object being imaged can be represented, as far as attenuation properties are concerned, by a combination of equivalent thicknesses of said basis materials.

If one chooses a type of material for the partially transparent body belonging to said group, the said body can be decomposed into a combination of two layers of equivalent thicknesses of said basis materials.

Based on the data of the calibration one can calculate the thickness of said body in function of an estimation of the radiation scatter signal at the position of said body in the image of the object and in function of the total signal (=primary radiation signal + radiation scatter signal) the one in said image under and near the position of said body.

The real radiation scatter signal is the signal for which the calculated body thickness is equal to the real thickness of said body.

Because of the limited spatial frequency of the radiation scatter, a limited amount of partially transparent bodies is required. One can, if desirable, not take into account the bodies under which the signal varies too much. After calculation of the radiation scatter signal in the image at the position of the chosen bodies, a radiation scatter surface is generated by interpolation and subtracted from said image.

Although the partially transparent bodies cause an extra drop of the primary radiation signal, the information about the object being imaged is not lost at the positions of the bodies

DESCRIPTION OF THE PREFERRED EMBODIMENTS

Figure 1:
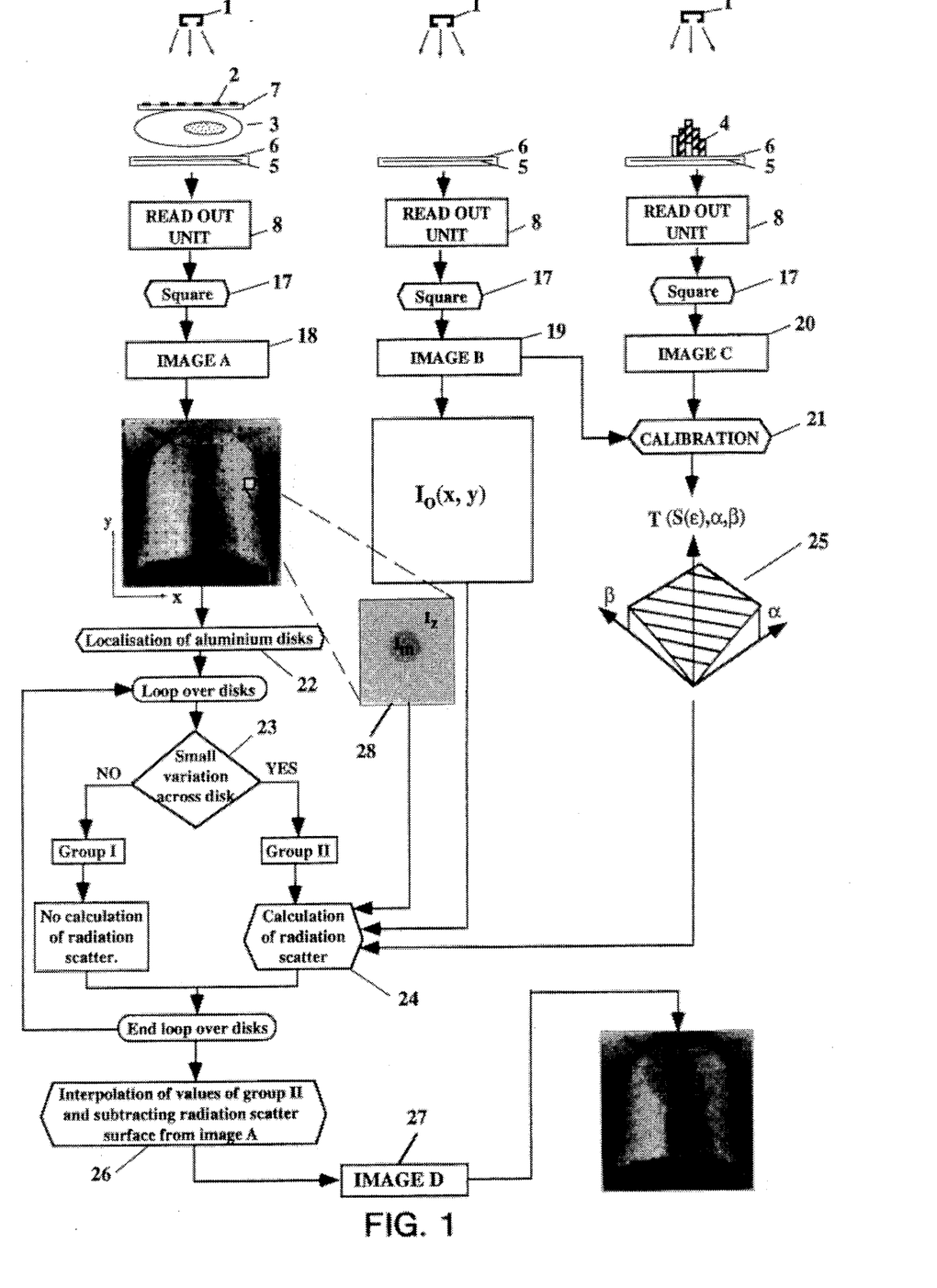
FIG. 1 gives a schematic representation of one x-ray imaging system in which the method according to the invention can be employed.

Generally, two basic preferred embodiments of a system and/or method according to the invention will be described, for monochromatic or quasi monochromatic x-radiation and for polychromatic x-radiation. FIG. 1 refers to the polychromatic case and FIG. 10 to the monochromatic case. We start with the polychromatic case.

FIG. 1 gives a schematic representation of an x-ray imaging system and a method for scatter compensation in accordance with the invention. The method and system of this embodiment are used in a preferred embodiment for polychromatic x-radiation of the source but can be used also for monochromatic x-radiation. In this embodiment an x-ray image of an object is made for which we want to calculate the scattered radiation component and a calibration is made that gives the effect of the beam hardening of the same photon energy spectrum as used for making the object image. The calibration data plus the signal in the image under a small partially transparent piece of matter plus the signal just besides the piece help to compensate said signal in the image under said small partially transparent piece of matter for scattered radiation; an equal estimated amount of scattered radiation is subtracted from both signals. Knowing the real thickness of the partially transparent piece of matter, the calibration data tell us whether the combination of the two compensated signals (=primary radiation signals) is possible or not; it is only approximately possible when the correct amount of scattered radiation was subtracted.

Referring to FIG. 1: x-radiation from an x-ray tube 1 (provided with its electronic control circuits which are not shown explicitly) is directed through a partially transparent shield (partially transparent for x-ray radiation) and through an object 3 towards a detector.

In this embodiment the partially transparent shield consists of a Lucite plate 7 of constant thickness with a plurality of aluminum cylinders 2 placed on it.

In this embodiment the detector consists of a sheet 5 covered with a layer of x-ray stimulable phosphors in a cassette 6 and of a read-out unit 8.

Generally in this text, by partially transparent shield is meant a plurality of for x-ray radiation partially transparent bodies of known materials and with known thicknesses (=thickness seen by an x-ray going straight from the source through said partially transparent body to the detector), distributed across the area above the object, between source 1 and object 3.

In the preferred embodiment of FIG. 1 plate 7 is used to hold the partially transparent bodies; other manners to keep the bodies in position are possible.

Essential for using the method according to the invention is that the thickness of a partially transparent body is known.

A Lucite plate 7 is chosen—other materials which are transparent for x-radiation are possible—because Lucite is a material that is hard enough to keep a constant thickness and to keep a plane shape as well as to attenuate as less as possible the x-ray radiation.

The partially transparent bodies 2 do not need to have the shape of a cylinder: in one preferred embodiment they have the shape of a cylinder and in another preferred embodiment they have the shape of a strip.

The material of these partially transparent bodies 2 does not need to be aluminum but in a preferred embodiment aluminum is used as material for these bodies in combination with the use of aluminum and polycarbonate as basis materials in the calibration system 4.

Further in this text it will become clear why this choice is preferred.

The screen is held in a cassette 6 which is opaque for light of the visible and the infrared range. The stimulable phosphors on the screen 5 have the property to get in a state of excitation after being exposed by x-ray radiation. The atoms in excitated state can emit, when they receive a light stimulus of a specific wavelength, light with different wavelengths when they return to their original state. The quantity of emitted stimulated light is proportional to the originally absorbed dose of x-ray radiation by the phosphors.

For reading of the latent image stored in the stimulable phosphor plate a read-out unit 8 is used which is based on opto-electronical reading techniques combined with digital writing in a computer.

In the embodiment of FIG. 1 we call detector the phosphor sheet 5 in the cassette 6 plus the read-out unit 8. Of course other types of detectors can be used.

Figure 2:
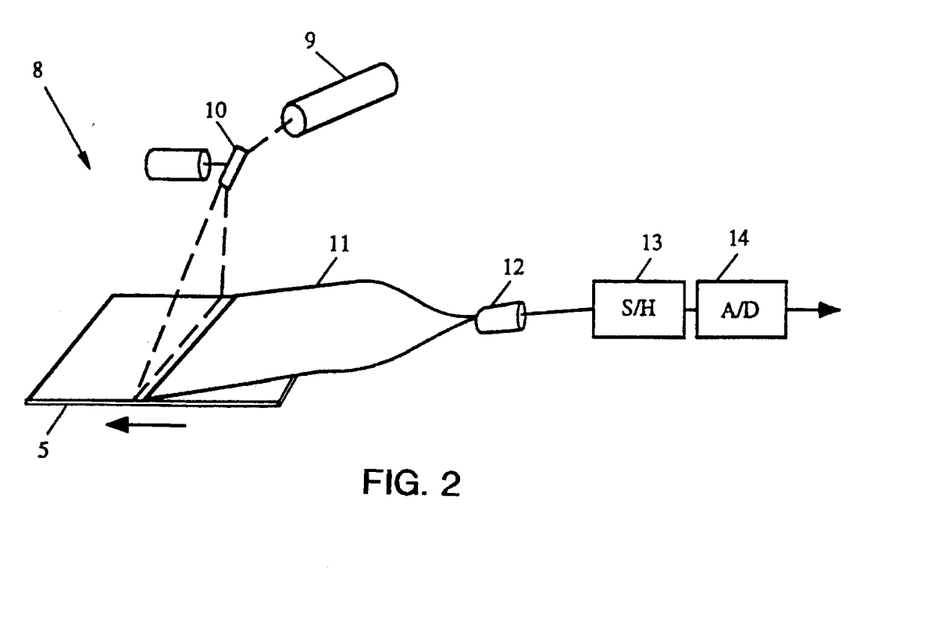
FIG. 2 gives a schematic representation of a read-out unit, i.e. a detector signal to electrical signal converter which can be used for the system according to the invention.

One embodiment of an image read-out unit is shown in FIG. 2. This figure shows a photostimulable phosphor sheet 5 that has been exposed to x-rays. In the radiation image read-out apparatus the latent image stored in the photostimulable phosphor sheet is readout by scanning the phosphor sheet with stimulating rays emitted by a laser 9.

The stimulating rays are reflected according to the main scanning direction by means of a galvanometric deflection device 10. The secondary scanning motion of performed by transporting the phosphor sheet in the direction perpendicular to the scanning direction. A light collector 11 directs the light obtained by stimulated emission onto a photomultiplier 12 where it is converted into an electrical signal, which is next sampled by a sample and hold circuit 13, and converted into a digital signal by means of an analogue to digital converter 14. The signal is also applied to a square root amplifier so that the output image representing signal also called 'original or raw' image is a signal which is proportional to the square root of applied exposure values and represents the pixel value in a large pixel matrix (for example 2048×2464 pixels).

Detection of Image of Object

Referring again to FIG. 1, the signal which is proportional to the square root of applied exposure values is squared 17 and gives the image of the object, IMAGE A 18, which represents a signal I (x, y) (in function of the pixel coordinates x and y of the image) which is proportional to the absorbed x-ray radiation by the phosphor sheet 5. The number of bits used for the values of I can be chosen according to the desired grey value resolution. In the embodiment of FIG. 1 a thorax is chosen as the object to be imaged. Of course other objects are possible.

Determination of Non-attenuated Photon Beam

In the embodiment of FIG. 1 a large part of the calculations will be done with the normalised intensity by means if meant the logarithm of the ratio of attenuated intensity to non-attenuated intensity.

In this context is meant by 'attenuated intensity' the x-ray radiation (in function of the pixel coordinates (x, y)) which is absorbed by the stimulable phosphor sheet 5 in cassette 6 in case the object 3 and the partially transparent shield (2, 7) are positioned between source 1 and cassette 6, and by the 'non-attenuated intensity' the x-ray radiation that would be absorbed by the stimulable phosphor sheet 5 in cassette 6 in case no object 3, neither a partially transparent shield (2, 7), neither any other object is positioned between source 1 and cassette 6. Often this non-attenuated photon beam cannot be measured or calculated properly in another way than by making an apart image.

For that reason in a preferred embodiment, a second image is made with exactly the same type of detector and source and source parameters (kV, mAs, focusing) as for IMAGE A 18 and with exactly the same relative position of the source 1 to the stimulable phosphor sheet 5 in the cassette 6. The read-out unit and the square unit convert the stored x-ray radiation of the sheet 5 to an image IMAGE B 19 that represents a signal $I_o(x,y)$ (in function of the pixel coordinates x and y of the image) which is proportional to the x-ray radiation absorbed by the phosphor sheet 5, with the same proportionality factor as for IMAGE A 18. Normally IMAGE B 19 is made just after or before IMAGE A 18, but this is not necessary.

Calibration

According to the invention, a calibration is made which allows to calculate accurately the radiation scatter signal in the image IMAGE A 18 of the object at the locations of the partially transparent bodies, which are indicated by 2 in the embodiment of FIG. 1. The calibration is especially useful for but not limited to medical applications.

In the same embodiment of FIG. 1 a third image is made for this purpose, IMAGE C 20. As said before this calibration must allow to calculate accurately the radiation scatter signal in the IMAGE A 18 in the locations of the partially transparent bodies.

In one embodiment (illustrated in FIG. 1) the image is made in the same way as given above for IMAGE A 18 and IMAGE B 19, but in this case the object being imaged is a combination of thicknesses 4 of two different materials which have a different x-ray absorption behaviour. These two materials belong to the group of materials that interact by approximately two physical processes with x-ray photons of energies of the range of most x-ray tubes: through Compton scatering and through photoelectrical absorption.

As known from the prior state of the art, two materials of this group can be chosen as basis materials which means here that the x-ray attenuation coefficients of all the other materials of the group can be found by a linear combination of those of the two basis materials.

For medical applications, in a preferred embodiment, the two basis materials are often chosen to be a soft tissue equivalent material respectively a bone equivalent material. Other materials can be chosen as basis materials.

It is advantageous to use a so-called calibration phantom for the purpose of generating calibration data.

A radiographic phantom suitable for generating the required calibration data generally comprises (a) a set of containers, preferably cylindrical containers, that are positioned in between the area detector and the x-ray source, (b) a number of combinations of basic materials of different thicknesses provided in each of said containers, (c) a frame for holding said containers in such a position that each of the containers is directed towards the x-ray source.

In one embodiment this calibration phantom comprises 36 cylindrical containers, that are filled with a number of combinations of thicknesses of basic materials. In this embodiment the basic materials are aluminum and polycarbonate.

The frame for holding the containers and directing them towards the radiation source consists of two parallel positioned plates.

A first so-called baseplate has a number of recesses into which the cylindrical containers fit.

The baseplate is preferably a metallic plate provided with a lead layer in between the recesses so that x-rays cannot penetrate through the plate at locations in between the containers and hence cannot expose the detector to scatter.

At a given distance above this plate, in this example this distance is equal to 12 cm, a second plate, referred to as supporting plate, is provided. The supporting plate has a number of holes through which the cylindrical containers are directed. The position of the holes in the support plate together with the position of the support plate relative to the base plate provide that the cylindrical containers are all directed towards a source of irradiation.

In one embodiment the cylindrical containers were directed towards a single point located at a known distance, in this example 150 cm, measured above the center of the baseplate.

The supporting plate can be held above the baseplate by means of a fixed connection.

Alternatively the support plate is movable. A movable support plate is preferred in case calibration data are to be obtained for different positions of the radiation source, i.e. for a set of distances between a source of irradiation and a detector.

A movable support plate provides that the direction into which the cylindrical containers point, can be changed hereby enabling that the containers are directed towards a source of irradiation positioned at a several distinct distances within a given range of distances.

The support plate can be fixed for a certain distance of the irradiation source relative to the frame and can be changed for other distances within the given range.

For example, when the distance between source of irradiation and detector is doubled, the distance between the base plate and the support plate is likewise to be doubled in order to have the cylindrical containers point at the irradiation source.

The change of the angle between the base plate and the axis of the cylindrical containers that are farest away from the center of the base plate which occurs due to the displacement of the support plate, is relatively small. The change of the diameter of the openings in the support plate which is required when changing the distance between base plate and support plate is consequently also relatively small and can be bridged by a non-rigid fixing of the containers in the base plate. This non rigid fixing can for example be realised by means of an elastically deformable substance positioned in the recessed in the base plate inbetween the cylinders and the base plate.

The inner wall of the containers is preferably provided with a lead layer so that scattered radiation cannot penetrate through the walls inside the containers.

Also on top of the upper material in the containers, i.e. the material that faces the source of irradiation a lead beam stop is provided, said beam stop only covering part of the upper surface of the upper material. This lead beam stop provides a measurement of the scattered radiation under the beam stop.

Indeed, since in this application one is only interested in the attenuation by x-rays by a combination of thicknesses of basic materials, the influence of scattered radiation is to be eliminated. For this purpose, a cylindrical lead beam stop is provided in the center of the surface of the upper basic material in each cylindrical container.

Next, the scattered radiation in the shadow of the lead beam stop is measured and subtracted from the signal detected in the neighborhood of the lead beam stop.

To provide an accurate measurement it is necessary that the dimensions of the section of the containers and of the pieces of basic material is adequately large.

Preferably the diameter of all of the cylindrical containers is identical. The basic materials are preferably provided in a cylindrical form having a diameter that is slightly smaller than the diameter of the container so that the material fits very well inside the container.

In the embodiment of FIG. 1 the calibration image IMAGE C 20 is combined with IMAGE B 19 to generate the calibration data 25. The signals $I_o(x,y)$ of IMAGE B 19 are used to calculate the ratio of the attenuated intensity signal and the non-attenuated intensity signal (=in case no calibration phantom is positioned between source and detector) for a certain thickness combination of the basis materials. The negative logarithm of this ratio is represented in 25 by $T(S(\epsilon),\alpha,\beta)$, where $S(\epsilon)$ is the spectrum of the source (representing the relative distribution of the photon energies) in function of the photon energy $\epsilon$, $\alpha$ and $\beta$ being the thicknesses of the two basis materials. Given the name 'attenuation' to the parameter T, it can be mentioned that T gives for said spectrum $S(\epsilon)$ the attenuation in function of the thicknesses of the basis materials. More generally speaking, if a detector is used of which the absorption of x-ray radiation is energy dependent with abs ($\epsilon$) representing its absorption coefficient in function of the photon energy $\epsilon$, one can say that T depends on the 'total' spectrum $S'(\epsilon)=S(\epsilon)\cdot abs(\epsilon)$. T is then given by the relationship:

$$T(\alpha,\beta) = -\ln\left[\frac{\int_\epsilon S(\epsilon)\cdot abs(\epsilon)\cdot \exp(-\mu_\alpha(\epsilon)\cdot\alpha - \mu_\beta(\epsilon)\cdot\beta)d\epsilon}{\int_\epsilon S(\epsilon)\cdot abs(\epsilon)\cdot d\epsilon}\right]$$

where $\mu_\alpha(\epsilon)$ and $\mu_\beta(\epsilon)$ are the linear attenuation coefficients of the two basis materials.

The x-ray absorption of the described photostimulable phosphor sheets is indeed energy dependent and for simplicity we'll speak about the spectrum always keeping in mind the contribution of the energy dependent absorption coefficient of the detector.

In a preferred embodiment the calibration data are fit to an analytical function $F(\alpha,\beta)\approx T(\alpha,\beta)$ of the thicknesses of the basismaterials. An example of such an analytical function $F(\alpha,\beta)$ (as proposed in Cardinal HN, Fenster A. Analytical approximation of the log-signal and log-variance functions of x-ray imaging systems, with application to dual-energy imaging, Med. Phys. 18(5), Sept/Oct. 1991, 867–879) is:

$$F(\alpha,\beta) = a_0\cdot\alpha + a_1\cdot\beta - \frac{a_2\cdot\alpha^2 + a_3\cdot\alpha\beta + a_4\cdot\beta^2}{1 + a_5\cdot\alpha + a_6\cdot\beta}$$

where the parameters $a_i$ (i=0, 1, ..., 6) depend on the used spectrum and detector and can be calculated in a fitting procedure, for example with the help of the Levenberg-Marquardt algorithm for non-linear least squares problems (Gill PE, Murray W., Wright MH. Practical optimization (Academic, London, 1981), pp. 136–137, 140–141). The model $F(\alpha,\beta)$ is very acurate and allows more precise calculations of the scattered radiation signals according to the invention. There are other models possible which also satisfy; the given model is just an example.

In another embodiment the calibration can be done independent from the object imaging, but the same spectrum of the photon energy as for the object must be used and the same type of detector. When several kinds of objects 3 are imaged by the source 1 with the same spectrum of the source and with the same type of detector, for all these images only one calibration is needed, one can use always the same calibration data.

Although in a preferred embodiment a calibration is made as described above, all alternative manners to obtain the attenuation in function of thicknesses basis material for the spectrum S' ($\epsilon$) may be used.

For the preferred embodiment, in which aluminum ($\beta$) and polycarbonate ($\alpha$) are used as calibration materials and aluminum disks are used as partially transparent bodies and a part of a human or animal body is used as object to be imaged, it will be illustrated how the scattered radiation signal can be calculated in a position 28 of the shadow of a disk in the image IMAGE A 18. For other objects, other basis materials and other partially transparent bodies the way of calculating stays essentially the same.

In a certain position (x,y) of IMAGE A 18, the object can be represented by a combination of thickness aluminum ($\beta$) and thickness polycarbonate ($\alpha$) (as mentioned before). This combination gives the same attenuation (if no scattered radiation is being considered) as the object in said position (x,y), independent from the source and from the detector.

For a disk 28 the signal in the image IMAGE A18 under the disk, represented by $I_z$ in FIG. 1 and the signal just besides the disk, represented by $I_m$, have approximately the same scattered radiation component $I_s$ if the radius of the disk is small enough. Another schematic representation of the intensities under and besides the disk is given in FIG. 11. In that figure the disk 2 and the object 3 are shown (the Lucite plate is not shown explicitly because it can be seen as a part of the object) with under it the intensities $I_z$ and $I_m$ and the scatter radiation component $I_s$. The scattered radiation component is a very low frequency component compared with the primary radiation component. If this scattered radiation component $I_s$ is subtracted from both signals $I_z$ and $I_m$, the difference between the two signals $(I_z-I_s)$ and $(I_m-I_s)$ is caused by the extra attenuation through the aluminum disk. Speaking in terms of basis materials, the object plus the aluminum disk above it can be represented by basis material thicknesses $(\alpha, \beta_z+d)=(\alpha, \beta_m)$, thickness of aluminum plus the basis material thicknesses of the object without the disk $(\alpha, \beta_z)$.

If the two signals $(I_z-I_s)$ and $(I_m-I_s)$ are divided by the signal $I_o$ in the position of the disk and if we take the negative logarithm of $(I_z-I_s)/I_o$ and of $(I_m-I_s)/I_o$, represented by $T_z$ respectively $T_m$, then these attenuation values $T_z$ and $T_m$ are equal to the attenuation values caused by $(\alpha, \beta_z)$ respectively $(\alpha, \beta_m)$.

Figure 3:
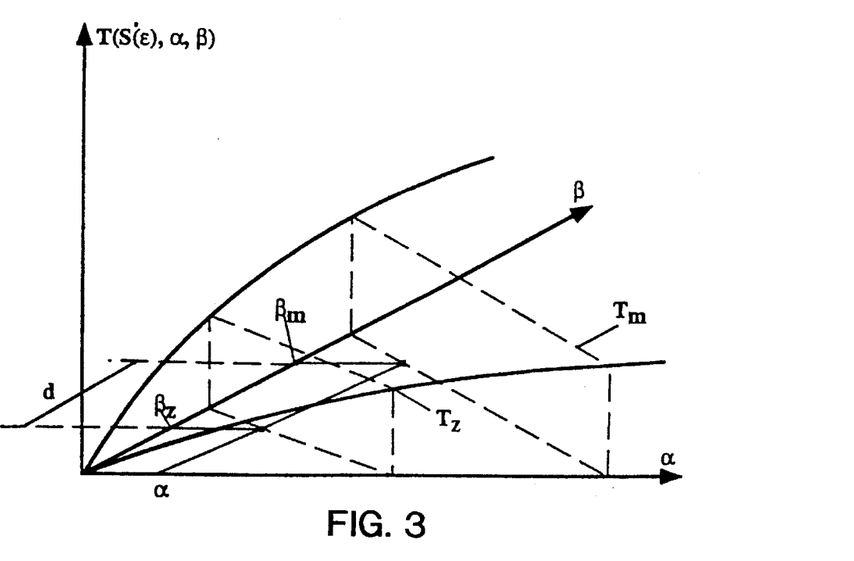
FIG. 3 gives the representation of the attenuation of the x-ray radiation in function of the thicknesses $\alpha$ and $\beta$ of the basis materials, used in the calibration procedure according to the invention.

This fact is illustrated in FIG. 3: T represents the attenuation in function of the thicknesses $\alpha$ and $\beta$ of the basis materials for the used source spectrum S ($\epsilon$) and detector with absorption coefficient abs($\epsilon$). For said basis material thicknesses $(\alpha, \beta_z)$ and $(\alpha, \beta_m)$ the corresponding attenuation values $T_z$ and $T_m$ are shown, as well as the thickness d of the partially transparent aluminum body.

Referring again to FIG. 1, the calculation 24 of the scattered radiation component $I_s$ of the signal in IMAGE A 18 in the position of the partially transparent body is based on the following idea, which is essential for the method according to the invention.

The thickness d of the partially transparent body is known and if we assume a certain value $I_{s\_est}$ as an estimation of the scattered radiation component of IMAGE A 18 in the position of the partially transparent body then $I_{s\_est}=(I_s+\Delta I_s)$ being a wrong estimation of $I_s$ with absolute error $\Delta I_s$.

If subtract this $I_{s\_est}$ from both measured signals $I_z$ and $I_m$, then the combination of $I_{zd\_est}$ ($=I_z-I_{s\_est}$) and $I_{md\_est}$ ($=I_m-I_{s\_est}$) is possible if the shield has another thickness than the real one if $\Delta I_s$ is not zero, as will be shown further in this text.

The calibration data allow us the calculate the thickness d_c of the partially transparent body in function of the values $I_{zd\_est}$ and $I_{md\_est}$.

Well, using the calibration data, calculate (given the value of $\alpha$) for different estimations of the scattered radiation component $I_{s\_est}$ the corresponding thickness d_c of the shield until a combination of $I_{zd\_est}$ and $I_{md\_est}$ is found such that the calculated thickness d_c of the shield equals the real one d.

Figure 4:
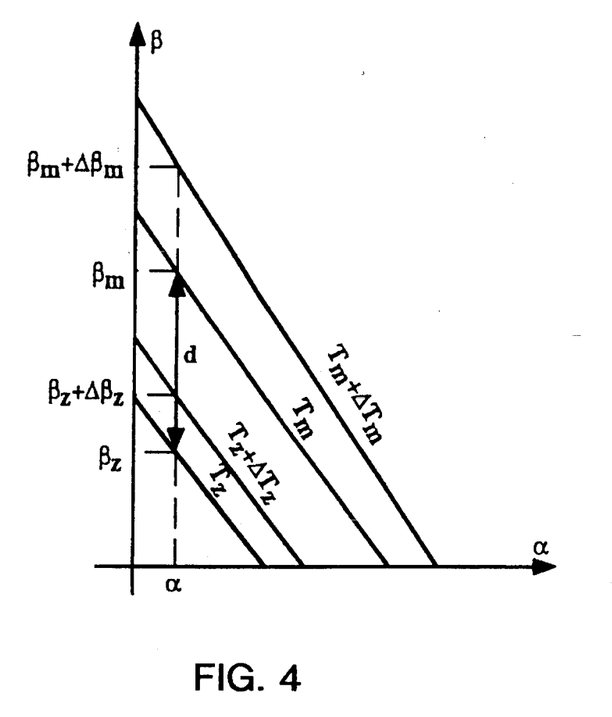
FIG. 4 gives another representation of FIG. 5 and illustrates the calculation, according to the invention, of the thickness of a partially transparent body of the same material as $\beta$.

In the preferred embodiment, using aluminum for the partially transparent bodies and a calibration with aluminum and polycarbonate, we can calculate the thickness of the shield as follows:

FIG. 4 illustrates the calculation. In order to clarify the calculations we first need to show that (d_c–d) is a monotone increasing function of the estimation $I_{s\_est}$ (or of the error $\Delta I_s$). For a certain thickness $\alpha$ of a polycarbonate we calculate the attenuation $(T_z+\Delta T_z)$ and $(T_m+\Delta T_m)$ in function of the estimated scattered radiation component $I_{s\_est}$. Using $I_{dz}=I_z-I_s$ and $I_{dm}=I_m-I_s$ and assuming that $\Delta I_s \ll I_{dz}$ one can write:

$$I_{dz\_est} = I_z - I_{s-est} = I_z - (I_s + \Delta I_s) = I_{dz} - \Delta I_s \text{ and}$$

$$T_z + \Delta T_z = -\ln\left(\frac{I_{dz_{est}}}{I_o}\right) = -\ln\left(\frac{I_{dz} = \Delta I_s}{I_o}\right) \approx$$

$$-\ln\left(\frac{I_{dz}}{I_o}\right) + \frac{\Delta I_s}{I_{dz}} = T_z + \frac{\Delta I_s}{I_{dz}}$$

The difference in aluminum thickness (FIG. 4) $\beta_m+\Delta\beta_m - (\beta_z+\epsilon\beta_z)$ equals the calculated thickness d_c of the aluminum disk. It can be easily proved that this thickness d_c minus the real thickness d is a monotone increasing function of the estimated scattered radiation component $I_{s\_est}$. For a certain equivalent thickness $\alpha$ polycarbonate a shift $\Delta T$ corresponds to a shift $\Delta\beta$. For small values of $\Delta T$ one has:

$$\frac{\Delta T}{\Delta \beta} \approx \frac{\delta T(\alpha,\beta)}{\delta \beta}, \text{ and}$$

$$\Delta \beta \approx \frac{\frac{\Delta I_s}{I_o}\exp(T)}{\left(\frac{\delta T(\alpha,\beta)}{\delta \beta}\right)_{(\alpha,\beta)}}$$

This is valid for the signal under and beside the disk. In the embodiment of FIG. 1 the calibration data are fit to an analytical function T ($\alpha,\beta$) (as mentioned before) so that the derivatives of T can be calculated analytically. Although this is not a strict demand, this leads to a higher accuracy.

We have for (d_c–d):

$$d\_-d=(\beta_m+\Delta\beta_m)-(\beta_z+\Delta\beta_z)-(\beta_m-\beta_z)=\Delta\beta_m-\Delta\beta_z$$

The values of $(\beta_m+\Delta\beta_m)$ respectively of $(\beta_m-\Delta\beta_z)$ for a certain value of $\alpha$ are found by searching in the calibration data for the unite value of $\beta$ which corresponds to $(T_m+\Delta T_m)$ respectively to $(T_z+\Delta T_z)$.

Further one has:

$$d\_c - d = \frac{\Delta I_s}{I_0} \left\{ \frac{\exp(T_m)}{\left(\frac{\delta T(\alpha,\beta)}{\delta \beta}\right)_{\alpha,\beta_m}} - \frac{\exp(T_z)}{\left(\frac{\delta T(\alpha,\beta)}{\delta \beta}\right)_{\alpha,\beta_z}} \right\} = \Delta I_s \cdot K$$

where K is a positive constant factor since $\exp(T_m) > \exp(T_z)$ and $$\left(\frac{\delta T(\alpha,\beta)}{\delta \beta}\right)_{\alpha,\beta_m} < \left(\frac{\delta T(\alpha,\beta)}{\delta \beta}\right)_{\alpha,\beta_z}$$

Figure 5:
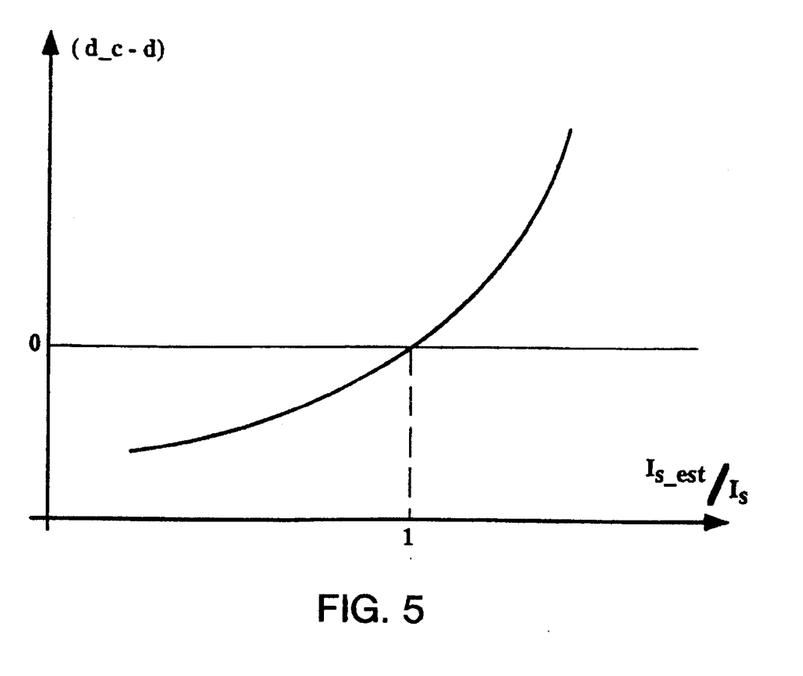
FIG. 5 illustrates the typical relationship between the calculated thickness of the partially transparent body and the estimated scattered radiation signal.

For larger values of $\Delta I_s$ the relation between $(d\_c-d)$ and $I_{s\_est}$ is not linear anymore but has a typical shape as shown in FIG. 5 where $I_s$ is the real scattered radiation signal.

Calculation of the Scattered Radiation Coefficient

So, referring back to FIG. 4, the calculation of the scattered radiation component $I_s$ is done as follows. If we calculate $(d\_c-d)$ for the correct value of $\alpha$ and for different estimates of $I_{s\_est}$, the zero crossing of the function $(d\_c-d)$ versus $I_{s\_est}$ gives the value of $I_s$.

For the calculation of $(d\_c-d)$, in the preferred embodiment of FIG. 1, for the values of $T(\alpha,\beta)$ or of the derivatives of $T(\alpha,\beta)$ the values of the analytical function $F(\alpha,\beta)$ and the derivatives of $F(\alpha,\beta)$ are used. To an estimate of $I_{s\_est}$ of the scattered radiation component correspond values $(T_m+\Delta T_m)$ and $(T_z+\Delta T_z)$.

For a particular value of $\alpha$ we have then:

$$T_m+\Delta T_m \approx F_m+\Delta F_m = F(\alpha,\beta_{m\_est}) = F(\alpha,\beta_m+\Delta\beta_m)$$

$$T_z+\Delta T_z = F_z+\Delta F_z = F(\alpha,\beta_{z\_est}) = F(\alpha,\beta_z+\Delta\beta_z)$$

There is only one solution for $\beta_{m\_est}$ and only one for $\beta_{z\_est}$. Finding the value of $\beta_{z\_est}$ ($\beta_{m\_est}$) can be done by dividing the $\beta$ axis in small intervals $\beta_{i=i^* \delta}$ ($i=0, 1, \ldots$) and calculating the values of $F(\alpha,\beta_i)$. The next step is to search the intervals $[i_z^* \delta, (i_z+1)^* \delta]$ and $[i_m^* \delta, (i_m+1)^* \delta]$ for which:

$$F(\alpha,i_z^*\delta) \leq F_z+\Delta F_z < F(\alpha, (i_z+1)^*\delta)$$

$$F(\alpha,i_m^*\delta) \leq F_m+\Delta F_m < F(\alpha, (i_m+1)^*\delta)$$

The values of $\beta_{z\_est}$ and of $\Delta_{m\_est}$ are calculated by linear interpolation. The value of $(\beta_{m\_est} - \beta_{z\_est})$ is equal to $(d\_c-d)$ for $I_{s\_est}$ and for $\alpha$. For different values of $I_{s\_est}$, covering the scope of expected possible scatter fractions, $(d\_c-d)$ is calculated in the same way. It has been shown before that the function $(d\_c-d)$ is a monotone increasing function of $I_{s\_est}$. So, with the said values of $I_{s\_est}$, for which $(d_{13} c-d)$ is calculated, and with the values of $(d\_c-d)$, a curve is fitted by a linear interpolation technique and the zero crossing gives the value of the scattered radiation component $I_s$.

To obtain the correct value of $I_s$ we need to know more or less what the equivalent thickness $\alpha$ of polycarbonate is at the position of the disk. We can estimate $\alpha$ based on the measured signal $I_z$ in IMAGE A 18 near the disk. For medical applications $\alpha$ is an indication for the thickness of the soft tissue. In a preferred embodiment the source spectrum is not too broad and in that case the estimation of $\alpha$ is less critical for the calculations. A rough estimation of the value of $\alpha$ may cause only a relatively small error of the calculated scattered radiation component $I_s$.

Figure 6:
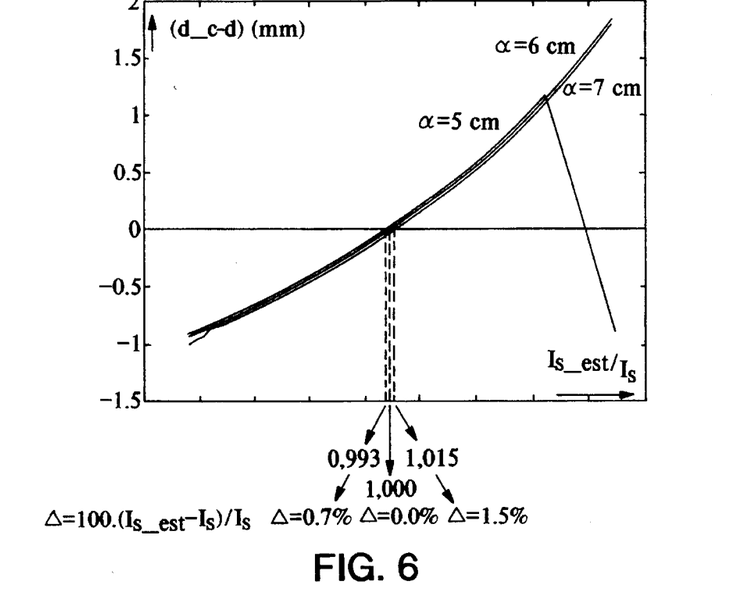
FIG. 6 gives an example of a spectrum of an x-ray source that can be used for an x-ray imaging system in which the method according to the invention can be used.
Figure 7:
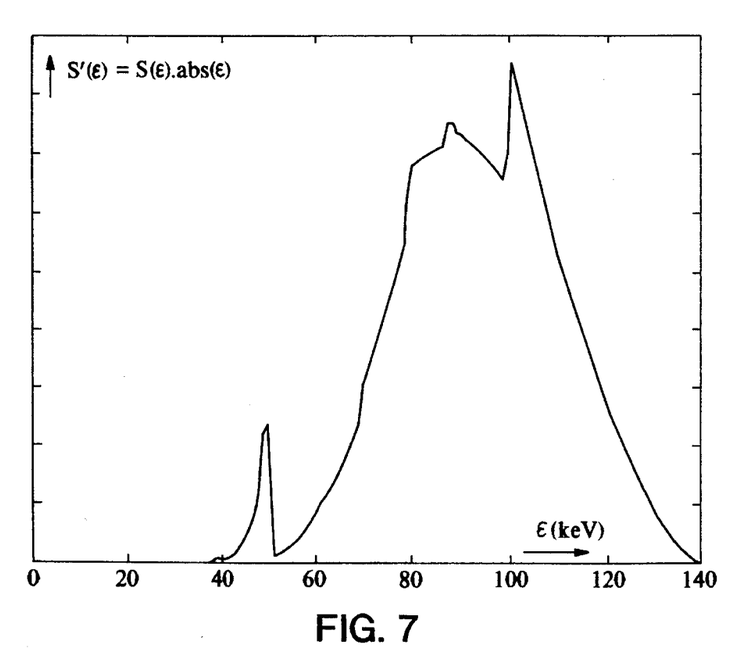
FIG. 7 gives an example of the relationship between the thickness of the partially transparent body, the equivalent thickness $\alpha$ of the basis material and the estimated scatter radiation signal.

This is illustrated in FIG. 6 and FIG. 7.

FIG. 7 shows a possible spectrum of a conventional x-ray source, used at 140 kV and filtered with 0,3 g/cm² Gadolinium and 1 mm Cu. $S(\epsilon)$ is the source spectrum filtered by the gadolinium and copper and $abs(\epsilon)$ is the absorption coefficient of the detector (in this example being a photostimulable phosphor sheet) in function of the photon energy $\epsilon$.

FIG. 6 shows the relation between the calculated thickness $d\_c$ of an aluminum disk minus the real thickness $d$ versus the estimated scattered radiation signal $I_{s\_est}$. The spectrum of FIG. 7 was used for irradiation of 5 mm aluminum and 6 cm polycarbonate. The used partially transparent body used was an aluminum circular cylinder of thickness $d=4$ mm and diameter 3 mm. For values $\alpha=5$ cm, $\alpha=6$ cm and $\alpha=7$ cm the relation $(d\_c-d)$ vs. $(I_{s\_est}/I_s)$ is plotted. The percentile error $\Delta$ on $I_s$ caused by the wrong value of $\alpha$ in this particular case is very small.

Referring again to FIG. 1, before the scattered radiation component in IMAGE A 18 at the position of the disks can be calculated, the aluminum disks (more generally speaking the partially transparent bodies) are localised 22. This localisation can be done in different ways. The shape of the partially transparent bodies is known and segmentation of the areas in the 'shadow' of these said bodies is not very difficult. Once the disks are localised, in a preferred embodiment, for reasons of accuracy, only for those disks under which the signal doesn't vary too much 23, the scattered radiation component is calculated. After the calculation of the scattered component in the positions of the bodies, an interpolation 26 of the values of the scattered component in these positions generates a scattered radiation surface $I_s(x,y)$ that represents the scattered radiation component in all positions of the image. Subtracting this scattered radiation surface 26 from the IMAGE A 18 gives IMAGE D 27, the image of the object, compensated for scattered radiation.

The information about the object under a partially transparent body is not lost; the x-ray radiation signal is just extra attenuated by the body. The effect of the extra attenuation can be eliminated in a further step.

Figure 9:
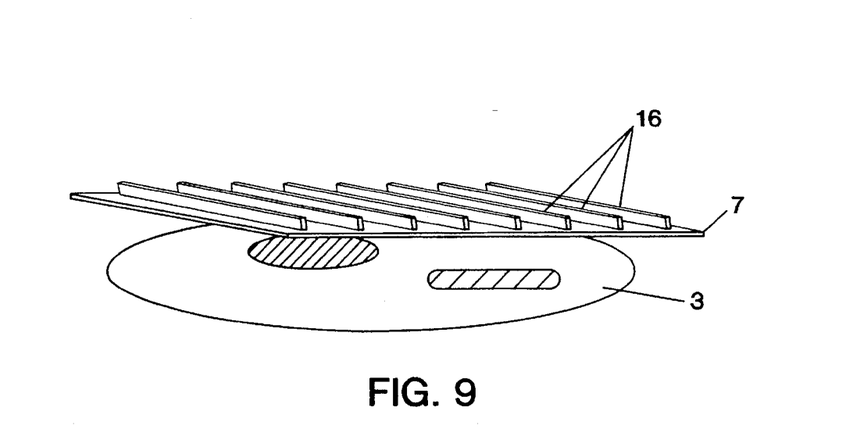
FIG. 9 gives the schematic representation of a possible partially transparent shield with which the method according to the invention can be employed.

Another good realisation of a partially transparent shield is shown in FIG. 9. The partially transparent bodies 16 in this embodiment are straight strips positioned parallel on a Lucite plate 7. One advantage of this embodiment is that the localisation in the image of the positions of the strips is more easy. We need enough $I_s$ data, covering the area of the detector, for an interpolation which gives an accurate estimate of the scattered radiation in the whole image. When a strip is used as partially transparent body it is easy to find enough $I_s$ data: we can choose easily positions on the strips for which we want to calculate the scattered radiation component in the image, neglecting the positions wherein the x-ray radiation signal varies too much because of sharp edges or other reasons.

In a preferred embodiment we use a reasonable large air gap between the object and the detector so that the spatial frequency of the scattered radiation signal is reduced as well as the amount of scattered radiation detected by the detector.

The accuracy of the method increases of course when the partially transparent bodies are directed as good as possible towards the source, perpendicular to the x-ray radiation falling on it, and when the bodies have everywhere the same thickness for this radiation (no smooth edges but sharp ones). In case aluminum is used as material for the partially transparent bodies it is preferred (in a preferred embodiment) that the height of the disks or strips (or other kind of bodies) have at least a height of 4 mm, in order to have enough contrast between the signal under the bodies and the signal beside the bodies.

The diameters of the bodies (the diameter of the disks, the width of strips, etc. . . . ) must not be too large. Otherwise the scattered radiation signal under the bodies is not equal to the scattered radiation signal beside the bodies. On the other hand the diameters must not be too small because noise and other artifacts have a great influence too on the measured signal under the bodies. It would be good that there are enough pixels under the bodies, so that a local mean value can be used for the signal under a body.

Figure 8:
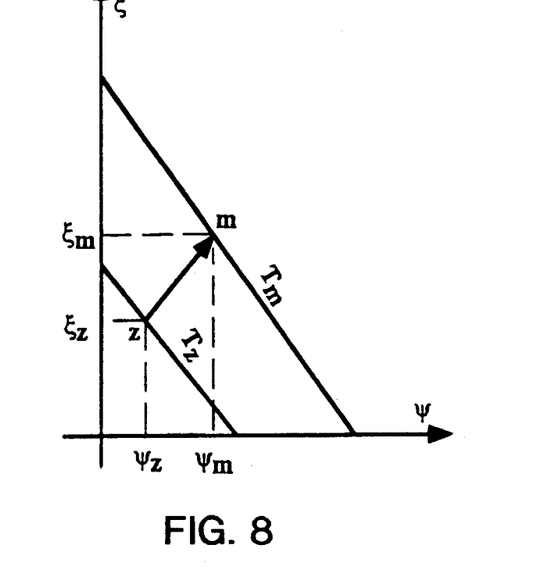
FIG. 8 illustrates the effect of a partially transparent body, made from another material than the basis materials for the calibration.

In the case that another material than aluminum is chosen for the calibration or for the material of the partially transparent body, the situation is very much analogue. In FIG. 8 the factor connecting z and m represents the equivalent thicknesses of the basis materials for the partially transparent shield. In the figure $\xi$ and $\psi$ are the thicknesses of the basis materials; the partially transparent body is made from another material then the basis materials and has thickness d. So the primary radiation signal $T_m$ detected besides said body in the way which is represented in the graph. In this case where another material than the basis materials is used for the partially transparent bodies, one has to estimate the two equivalent thicknesses basis material of the object at the position of the partially transparent body, before one can start the calculation of the scattered radiation component. Therefore, for reasons of accuracy, in a preferred embodiment a narrow photon energy spectrum is used for the imaging and a material of the partially transparent bodies is chosen which has a relatively small equivalent thickness of one basis material and a relatively large equivalent thickness of the other basis material.

After having explained in the last pages the preferred embodiment for polychromatic x-radiation, we treat the preferred embodiment for monochromatic x-radiation or quasi monochromatic x-radiation.

Figure 10:
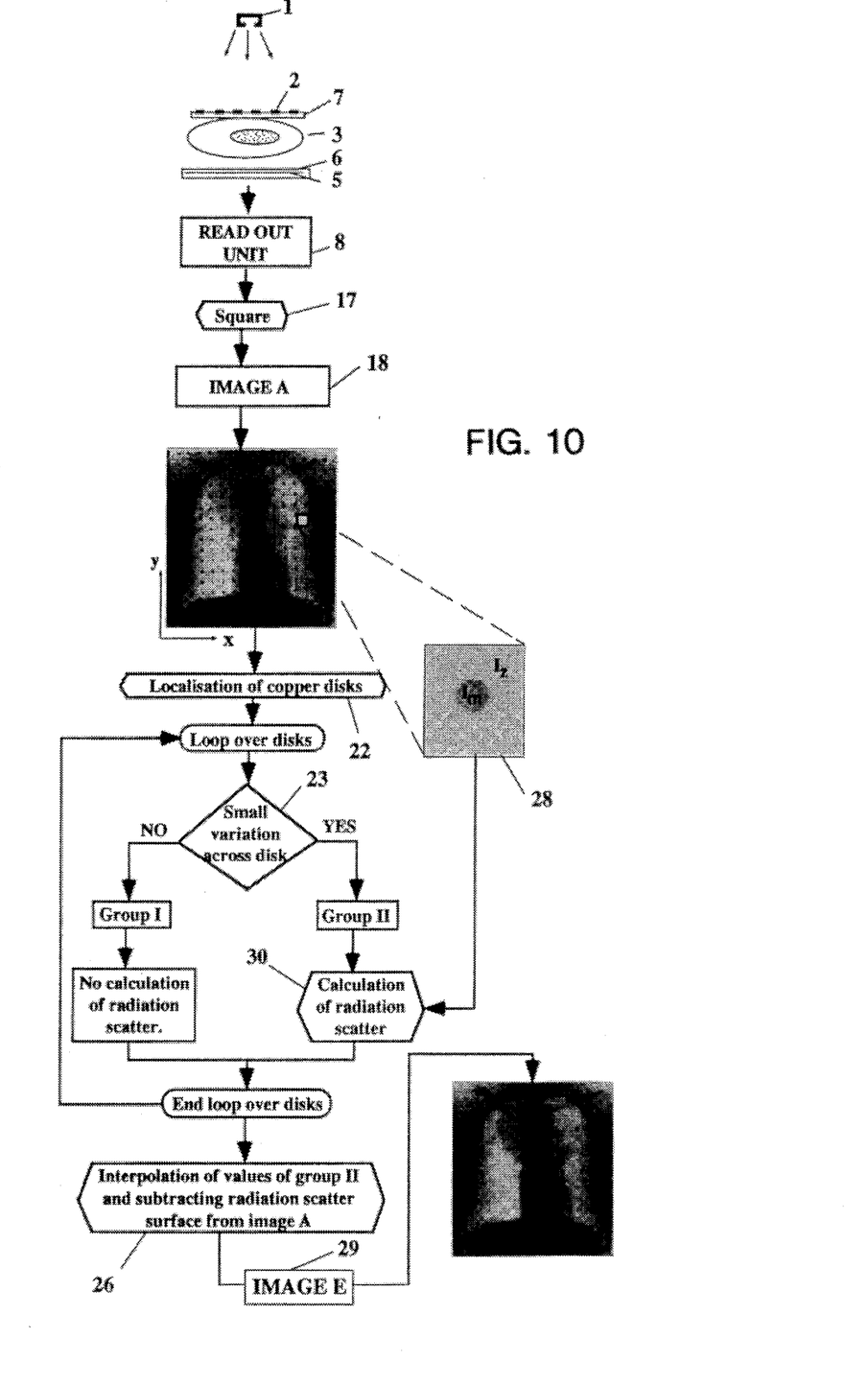
FIG. 10 is another schematic representation of another x-ray imaging system in which the method according to the invention can be employed.

FIG. 10 gives another schematic representation of an x-ray imaging system and a method for scatter compensation in accordance with the invention.

The method and system of this embodiment are used in an embodiment wherein monochromatic x-ray radiation is applied. This method can also be applied in case of polychromatic x-radiation with a narrow spectrum of the photon energies. In this case no calibration is made, the beam hardening for monochromatic x-ray radiation is zero and is small for very narrow x-ray spectra.

X-ray radiation source 1 is directed through a partially transparent shield (partially transparent for x-ray radiation), in a preferred embodiment consisting of a Lucite plate 7 of constant thickness with a plurality of copper cylinders 2 placed on it, and through an object 3 towards a detector, in this preferred embodiment consisting of a sheet 5 covered with a layer of x-ray stimulable phosphors in a cassette 6 and of a read-out unit 8.

As mentioned before, generally in this text, by partially transparent shield is meant a plurality of for x-ray radiation partially transparent bodies of known materials and with known thicknesses (=thickness seen by an x-ray going straight from the source through said partially transparent body to the detector), distributed across the area above the object, between source 1 and object 3.

In the preferred embodiment of FIG. 10 plate 7 is used to hold the partially transparent bodies; other manners to keep the bodies in position are possible. Essential for using the method according to the invention is that the thickness of a partially transparent body is known. A Lucite plate 7 is chosen—other materials which are transparent for x-ray radiation are possible—because Lucite is a material that is hard enough to keep a constant thickness and to keep a plane shape as well as to attenuate as less as possible the x-ray radiation. The partially transparent bodies 2 do not need to have the shape of a cylinder: in a preferred embodiment they have the shape of a cylinder and in another preferred embodiment they have the shape of a strip. The material of these partially transparent bodies 2 does not need to be copper but in a preferred embodiment copper is used as material for these bodies because the attenuation of x-ray radiation by copper is rather high so that the height of the copper disks can be limited, which has practical advantages.

The sheet 5 is held in a cassette 6 which is opaque for light of the visible and the infrared range. The stimulable phosphors on the sheet 5 have the property to get in a state of excitation after being exposed by x-ray radiation. The atoms in excited state can emit, when they receive a light stimulus of a specific wavelength, light with different wavelengths when they return to their original state.

The quantity of emitted stimulated light is proportional to the originally absorbed dose of x-ray radiation by the phosphors. For reading of the latent image stored in the stimulable phosphor sheet a read-out unit 8 is used which is based on opto-electronical reading techniques combined with digital writing in a computer.

In the embodiment of FIG. 10 we call detector the phosphor sheet 5 in the cassette 6 plus the read-out unit 8. Of course other types of detectors can be used.

One embodiment of an image read-out unit is shown in FIG. 2 which is already explained before.

Referring again to FIG. 10, the signal which is proportional to the square root of applied exposure values is squared 17 and gives the image of the object, IMAGE A 18, which represents a signal I(x,y) (in function of the pixel coordinates x and y of the image) which is proportional to the absorbed x-ray radiation by the phosphor sheet 5. The number of bits used to represent a value of I(x,y) can be chosen according to the desired accuracy. In the embodiment of FIG. 10 a thorax is chosen as the object to be imaged. Of course other objects are possible.

It will be shown how the scattered radiation signal can be calculated in a position 28 of the shadow of a disk in the image IMAGE A 18 for the embodiment of FIG. 10.

For a disk 28 the signal in the image IMAGE A 18 under the disk, represented by $I_m$ in FIG. 10 and the signal just besides the disk, represented by $I_z$, have approximately the same scattered radiation component $I_s$ if the radius of the disk is small enough.

Figure 11:
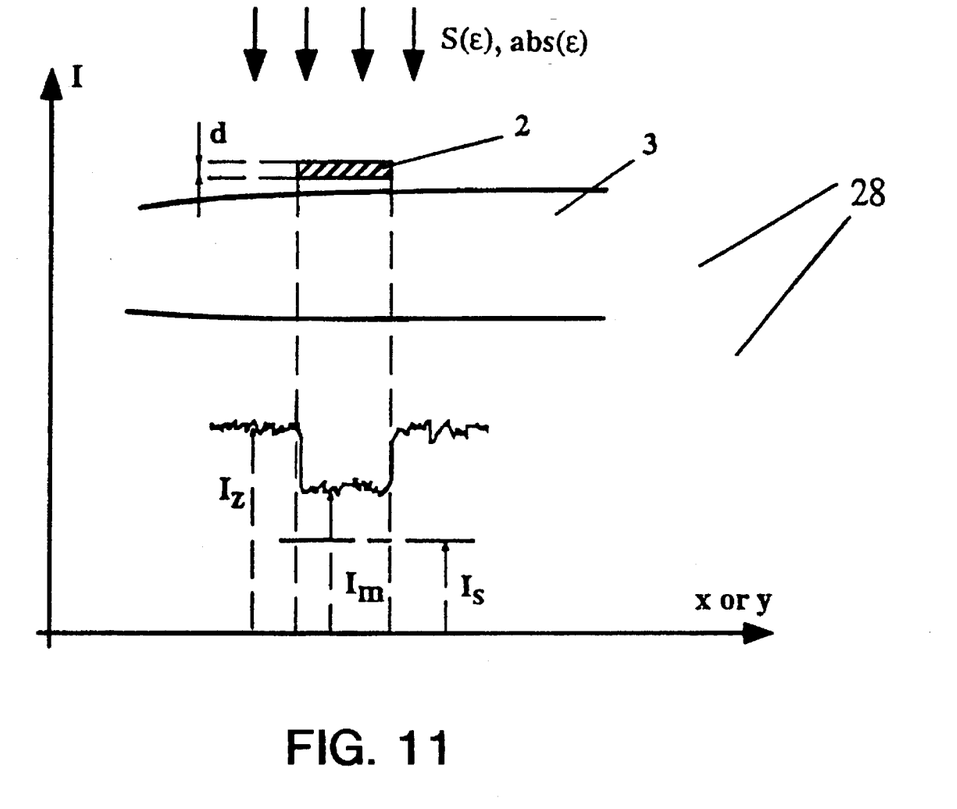
FIG. 11 illustrates the effect of a partially transparent body on the attenuation of the x-ray radiation.

Another schematic representation of the intensities under and beside the disk is given in FIG. 11.

In FIG. 11 the disk 2 and the object 3 are shown (the Lucite plate is not shown explicitly because it can be seen as a part of the object) with under it the intensities $I_z$ and $I_m$ and the scatter radiation component $I_s$. $S(\epsilon)$ is the spectrum of the x-ray radiation of the source and abs($\epsilon$) is the absorption coefficient of the detector. The scattered radiation component is a very low frequency component compared with the primary radiation component.

Referring again to FIG. 10, the spectrum $S(\epsilon)$ in a particular embodiment is narrowly concentrated around its mean energy $\epsilon_0$. If the scattered radiation component $I_s$ is subtracted from both signals $I_z$ and $I_m$, the difference between the two signals $(I_z-I_s)$ and $(I_m-I_s)$ is caused by the extra attenuation through the copper disk.

The calculation 30 of the scattered radiation component $I_s$ of the signal in IMAGE A 18 in the position of the partially transparent body is based on the following equations with the assumption that the mean energy of the photons is $\epsilon_0$ and that the spectrum is very narrowly concentrated around $\epsilon_0$:

$$(I_z - I_s) \cdot \exp(-\mu_d(\epsilon_0) \cdot d) \approx (I_m - I_s)$$

$$I_s = I_z - \frac{I_z - I_m}{1 - \exp(-\mu_d(\epsilon_0) \cdot d)}$$

In these equations $\mu_d(\epsilon_0)$ is the linear attenuation coefficient of the disk and $d$ is the thickness of the disk.

One can always make the factor $\exp(-\mu d(\epsilon_0) \cdot d)$ slightly dependent on the signal $I_z$, estimating it based on a first rough estimation of the scattered component and guessing what the effect of beam hardening can be. The influence of the beam hardening on the factor is larger when the spectrum is broader. The materials in object 3 cause the spectrum to shift to higher mean energies. The broader the spectrum is, the larger is the shift and the greater the variation of the factor. If the original spectrum has a higher mean energy $\epsilon_0$, then the shift is mostly relatively smaller because the derivate of the attenuation coefficient with respect to the energy is mostly (as it is for copper) smaller in the area of higher energies.

Referring to FIG. 10, before the scattered radiation component in IMAGE A 18 in the positions of the disks can be calculated, the partially transparent bodies are localised 22 and in a preferred embodiment only for those bodies under which the signal doesn't vary too much 23, the scattered radiation component is calculated, for reasons of accuracy. After the calculation of the scattered component in the positions of the bodies, an interpolation 26 of the values of the scattered component in these positions generates a scattered radiation surface $I_s(x,y)$ that represents the scattered radiation component in all positions of the image. Subtracting this scattered radiation surface 26 from the image A 18 gives Image E 29, the for scattered radiation compensated image of the object.

The information about the object under a partially transparent bodies is not lost; the x-ray radiation signal is just extra attenuated by the body. The effect of the extra attenuation can be eliminated in a further step.

In a preferred embodiment we use an airgap between the object and the detector so that the spatial frequency of the scattered radiation signal is reduced as well as the amount of scattered radiation detected by the detector.

The accuracy of the method increases of course when the partially transparent bodies are directed as good as possible towards the source, perpendicular to the x-ray radiation falling on it, and when the bodies have everywhere the same thickness for this radiation (no smooth edges but sharp ones). When copper is used as material for the partially transparent bodies, a limited height of cupper (for example 0.2 mm) is sufficient to have sufficient contrast between the signal under the bodies and the signal beside the bodies.

The diameters of the bodies (the diameter of the disks, the width of strips, etc.) may not be too large. Otherwise the scattered radiation signal under the bodies is not equal to the scattered radiation signal besides the bodies. On the other hand the diameters must not be too small because noise and other artifacts have a great influence too on the measured signal under the bodies. It is good that there are enough pixels under the bodies, so that a local mean value can be used for the signal under a body.

We claim:

1. A method of generating a scatter-compensated radiographic image of an object comprising the steps of:

1) exposing said object together with a shield placed between a source of radiation and said object to an amount of radiation emitted by said source so as to generate a radiation image, said shield comprising a number of bodies of a known material and of a known thickness that are partially transparent to irradiation,
 2) detecting said radiation image by means of an area detector,
 3) converting the detected radiation image into an electrical signal representation,
 4) in a number of locations of said bodies within said radiation image deriving a signal proportional to the amount of scattered radiation,
 5) composing a scatter image representing in each location of the radiation image of said object the amount of scatter present in the radiation image by interpolation between derived scatter signal values,
 6) subtracting said scatter image from said electric signal representation of the detected radiation image so as to generate a scatter compensated radiographic image representation,
 7) applying said scatter-compensated image representation to an output device for generating a visible scatter-compensated image.

2. A method according to claim 1 wherein for a number of locations in a shadow of a partially transparent body, a signal value $I_m$ that is the electric signal representation of the radiation image in a location and a signal value $I_z$ that is the electrical signal representation of the radiation image in the neighbourhood of said shadow are generated, and wherein for each of said locations a scatter signal value is derived from $I_z$, $I_m$ and a damping factor of said partially transparent body.

3. A method according to claim 1 wherein said radiation image is detected by means of an area detector consisting of a photostimulable phosphor screen and wherein said radiation image is read out and converted into an electrical signal representation by scanning said screen by means of stimulating irradiation and by detecting the light emitted upon stimulation and converting the detected light into an electric signal.

4. A method according to claim 1 wherein said partially transparent bodies are made of copper.

5. A method according to claim 1 wherein said partially transparent shield is a Lucite plate of constant thickness holding a number of copper cylinders.

6. A method of generating a scatter-compensated radiographic image of an object comprising the steps of 1) exposing said object together with a shield comprising a number of bodies of a known material and of a known thickness that are partially transparent to irradiation, said shield being placed between an irradiation source and said object, to an amount of radiation emitted by said irradiation source, so as to generate a radiation image;
 2) detecting said radiation image by means of an area detector,
 3) converting the detected radiation image into an electrical signal representation,
 4) generating calibration data representing the attenuation of the spectrum of said irradiation source by combination of thicknesses of different basis materials,
 5) for a number of locations of said bodies estimating the scatter value on the basis of supplementary attenuation of primary irradiation photons by said bodies, 6) determining from the calibration data a thickness value of body material that corresponds with the estimated scatter value, 7) if said thickness value equals the thickness said body effectively has, then the estimated scatter value equals an effective scatter value and a scatter image is generated by interpolation in between effective scatter values in said locations, otherwise steps (5) to (6) are repeated, 8) subtracting the scatter image from said radiation image so as to generate a scatter-compensated image representation, 9) applying said scatter-compensated image representation to an output device for generating a visible scatter-compensated image.

7. A method according to claim 6 wherein a radiation image is detected by means of an area detector consisting of a photostimulable phosphor screen and wherein said radiation image is read out and converted into an electrical signal representation by scanning said screen by means of stimulating irradiation and by detecting the light emitted upon stimulation and converting the detected light into an electric signal.

8. A method according to claim 6 wherein said calibration data are generated by
   (1) exposing to a same spectrum of irradiation emitted by said irradiation source as used for exposure of said object a set of combinations of thicknesses of two basis materials selected from a group of materials such that the attenuation properties of a material can be deduced from attenuation caused by combinations of thicknesses of two of these materials so as to generate a calibration image,
   (2) detecting said calibration image by means of an area detector,
   (3) reading said calibration image in a number of predefined locations.

9. A method according to claim 8 wherein interpolation is applied to said calibration data.

10. A method according to claim 8 wherein said bodies of partially transparent material are made out of one of two basis materials selected for the purpose of generating calibration data.

11. A method according to claim 8 wherein the equivalent materials are a soft tissue equivalent and a bone equivalent material.

12. A method according to claim 8 wherein the equivalent materials are aluminum and polycarbonate and wherein a body is made out of aluminum.

13. A method according to claim 10 wherein said additional scatter signal caused by a body is obtained by performing the following steps:
   1) obtaining a signal value $I_m$ that is the electric signal representation of the radiation image at the location of said body and a signal value $I_z$ that is the electric signal representation of the radiation image at a location in the neighborhood of said body,
   2) for a set of estimated scatter signal values $I_{scat,est}$ calcuating corresponding attenuation values —ln and —ln, wherein $I_o$ represents non-attenuated irradiation emitted by said source,
   3) retrieving from the calibration data and an estimation of the equivalent thickness of the second basis material for the object at the location of said body a corresponding thickness $d_{scat}$ of the body, so as to find a value $I_{scat,est}$ for which $d_{scat}$ equals the thickness of the body, this value of $I_{scat,est}$ being equal to $I_{scat}$ in said location.

14. A method according to claim 13 wherein $I_o$ is obtained by means of said area detector the non-attenuated irradiation emitted by said source under identical exposure conditions as those used when exposing the object and the shield.

15. A method according to claim 6 wherein the equivalent thickness of the first basis material at the position of a body is obtained on the basis of the measured signal $I_z$ in the neighborhood of the body.

16. A method according to claim 6 wherein the extra attenuation by the partially transparent bodies is eliminated.

17. A method according to claim 6 wherein partially transparent bodies are straight strips of aluminum positioned parallel on a Lucite plate.

18. A method according to claim 6 wherein an air gap is provided between the object and the detector.

* * * * *